United States Patent [19]

Schultz

[11] Patent Number: 5,219,732

[45] Date of Patent: Jun. 15, 1993

[54] ANTIBODY-MEDIATED COFACTOR-DRIVEN REACTIONS

[75] Inventor: Peter G. Schultz, Oakland, Calif.

[73] Assignee: The Regents of the University of California, Oakland, Calif.

[21] Appl. No.: 554,004

[22] Filed: Jul. 17, 1990

Related U.S. Application Data

[63] Continuation-in-part of Ser. No. 402,848, Sep. 5, 1989, abandoned.

[51] Int. Cl.$^5$ .......................... C12P 1/00; C12P 17/18; C12N 9/00
[52] U.S. Cl. ...................................... 435/41; 435/119; 435/188.5; 435/189
[58] Field of Search ...................... 435/189, 183, 188.5, 435/41, 119; 530/387, 388

[56] References Cited

PUBLICATIONS

Shokat, K. M., et al, (1988) Angew. Chem. Int. Ed. Engl. 27 (9), 1172–1174.
Iverson, B. L., et al, (1989) Science 243, 1184–1188.
Blackburn, G. M. et al, (1989) Biochem J. 262, 381–390.

Primary Examiner—Charles L. Patterson, Jr.
Attorney, Agent, or Firm—Townsend and Townsend

[57] ABSTRACT

Chemical reactions capable of being rate-enhanced by auxiliary species which interact with the reactants but do not become chemically bound to them in the formation of the final product are performed in the presence of antibodies which promote the reactions. The antibodies contain regions within their antigen binding sites which recognize the auxiliary species in a conformation which promotes the reaction. The antigen binding site frequently recognizes a particular transition state complex or other high energy complex along the reaction coordinate, thereby promoting the progress of the reaction along the desired route as opposed to other less favorable routes. Various classes of reaction together with appropriate antigen binding site specificities tailored for each are disclosed.

8 Claims, 3 Drawing Sheets

ANTIBODY-MEDIATED COFACTOR-DRIVEN REACTIONS

This invention was made in part with support under Grant Contract No. C87-101226, awarded by the Department of Energy. The Government has certain rights in this invention.

CROSS REFERENCE TO RELATED APPLICATION

This application is a continuation-in-part of copending application Ser. No. 07/402,848, filed Sep. 5, 1989, now abandoned.

This invention lies in the general field of reactions relying on cofactors for the reactions to proceed, as well as the general field addressing the use of antibodies in chemical reactions for catalytic effect.

Commonly owned copending applications Ser. No. 07/273,455 and Ser. No. 07/273,786, both filed Nov. 18, 1988, and Ser. No. 07/341,783, filed Apr. 21, 1989, contain subject matter of possible relevance to the present invention. The experimental data in Example 1 was published in Shokat, K. M., et al., *Angew. Chem. Int. Ed. Engl.* 27(9): 1172-4 (1988).

BACKGROUND AND SUMMARY OF THE INVENTION

The scope of chemical reactions which rely on auxiliary species for promoting the reaction and/or directing its course is large and varied. The term "auxiliary species" is used herein to denote ions, molecules or complexes which interact with a substrate to promote its conversion, but do not become chemically bound to the substrate in the final product. Such reactions include those occurring both in and outside of the biological context.

One subset of these reactions are those in the biological context, where in the typical case the auxiliary species normally functions in coaction with a protein, which may be an enzyme or some other macromolecular species. The auxiliary species in such reactions is a cofactor or non-protein component which, in combination with the enzyme, enters into or promotes the reaction mechanism in any of a variety of ways. Cofactors of this type vary widely in chemical composition, including both organic and inorganic species, and including species which are loosely associated with the enzyme as well as prosthetic groups tightly associated with the enzyme. Other subsets of the reactions are reactions which do not occur as part of a biological process, with auxiliary species which are not biologically derived.

It has now been discovered that reactions involving the use of auxiliary species can be promoted by antibodies whose antigen binding sites have a conformation favorable to the reaction, either by increasing the reaction rate, improving the selectivity, or affecting some other parameter in a manner favorable to the progress of the reaction toward the desired product. The terms "antibody" and "antibodies" are used herein to include both whole antibodies and antibody fragments.

For those reactions which normally occur in the biological context, the antibodies in accordance with this invention serve as a replacement for enzymes, and function in combination with the cofactors to produce a result generally equivalent to that achievable with the enzymes. The antibodies thus function in a reaction-promoting manner analogous to the enzymes. The antibodies, like the enzymes which they replace, achieve this effect in a variety of ways, depending on the particular chemical reaction for which they are elicited and used. They may, for example, restrict the rotational and translational motions of the reacting species and/or cofactor, stabilize conformations of the reacting species and/or cofactor in a manner favorable to the reaction, stabilize transition state complexes of the reacting species and the cofactor, vary the electronic configuration of the reacting species and/or cofactor in a manner favorable to the reaction, or any other means of promoting the reaction.

In reactions normally occurring in contexts other than biological, the antibodies in accordance with this invention serve an analogous function, increasing the reaction rate, improving selectivity, or generally promoting the formation of products which might not otherwise be formed.

Reactions to which the present invention is applicable include both intramolecular and intermolecular reactions, including rearrangements, cyclizations, condensations, hydrolytic reactions, additions, eliminations, isomerizations, reductions and oxidations. Accordingly, substrates to which the present invention may be applied range in size from relatively small molecules of ten atoms or less to macromolecules such as proteins, hormones, polysaccharides and polynucleotides. Examples of such reactions are selective peptide and oligosaccharide hydrolysis, thiol oxidation, stereospecific alcohol oxidation, stereospecific ketone reduction, transamination reactions of keto acids to amino acids, glycosylation reactions, transacylation reactions of peptide esters, and phosphodiester hydrolysis.

Auxiliary species to which the present invention is applicable may likewise vary widely in size, ranging from monatomic metallic ions through small molecules of ten atoms or less to larger molecules with complex three-dimensional structures. As indicated above, the term "auxiliary species" is used herein to denote any species which, when used in accordance with the present invention, will function in coaction with an appropriate antigen binding site to promote the progress of a chemical reaction. The term "cofactor" will also be used in a general sense, to include all such auxiliary species.

Such species are not a part of the starting material or product, and may or may not undergo a change as the result of the reaction. These species, if used in conjunction with an enzyme rather than an antibody as in the present invention, would otherwise be termed "coenzymes," "activators," or "prosthetic groups," depending upon their structure and the means by which they are associated with the enzyme. Examples of such auxiliary species are nicotinamide coenzymes such as nicotinamide adenine dinucleotide (NAD) or its reduced form (NADH) or nicotinamide adenine dinucleotide phosphate (NADP), flavins, cobamides, cobalamins, ascorbic acid, ferredoxin, thiamine pyrophosphate, pyridoxal-based compounds such as pyridoxal phosphate, pyridoxol and pyridoxamine, tetrahydrofolic acid, biotin, S-adenosylmethionine, coenzyme A, purine phosphates, pyrimidine phosphates, glutathione, metal ions such as Cu, V, Fe, Zn and Co, and complexes of metal ions with ligands such as bipyridyl, phenanthroline, EDTA and porphyrins.

In the practice of the present invention, the auxiliary species are not covalently bound to the antibodies. The antibodies are thus formed separately from the auxiliary species, with binding sites which include regions which are complementary to the species in a manner which promotes the reaction by restricting the species to conformations, orientations, or electronic or steric characters which promote the progress of the reactions. In certain cases, the antigen binding sites are complementary to a transition state complex of the auxiliary species and the substrate, or any other high energy complex along the reaction coordinate leading to the reaction product.

Methods of eliciting antibodies for a particular reaction involve the use of a hapten designed to approximate the reactive moiety or moieties, including the auxiliary species itself as well as a substrate binding site, in the rotational, translational and electronic conformations needed for the reaction to proceed. In certain cases, the hapten will be a stable analogue of a transition state favorable to the reaction, the analogue being one in which an unstable portion of the structure has been replaced with a stable group of similar size, shape, orientation and electronic configuration. In further cases, the hapten will be a stable analogue that mimics an unstable intermediate on the reaction pathway. The analogue in such cases will be one which can be synthesized and isolated in high purity, unlike the intermediate itself. In still further cases, the hapten will be a hybrid or conjugated structure containing moieties analogous in steric and electronic conformation to the auxiliary species and the substrate. The arrangement of these moieties in the hybrid structure will closely approximate the actual auxiliary species and substrate in the relative orientation and spacing needed for the reaction to proceed. The present invention extends to still further types of haptens and the microenvironments which they create in the antigen binding sites, as will become apparent from the description which follows.

The present invention further entails in certain cases the discovery of stable haptens bearing the characteristics described above, and their use in eliciting the appropriate antibodies. In some of the reactions disclosed herein, the haptens are specifically designed to elicit antibodies which, although enhancing the progress of the reaction and the formation of the desired product, avoid product inhibition of the antibody binding capacity. This effect is also achieved in some cases by appropriate selection of the reactive species among alternative systems all of which are capable of forming the desired product. In some cases, antibodies will be generated to a specific isomer of the reacting species such that the products of the reaction have a stereocenter.

The use of the haptens in generating the antibodies follows conventional procedures involving host immunization. The haptens are generally coupled to carrier molecules which render them immunogenic, the coupling achieved through conventional linking groups or spacers. Further advantages in both quantity and specificity may be obtained by the use of monoclonal antibodies.

DETAILED DESCRIPTION OF THE INVENTION AND PREFERRED EMBODIMENTS

Figure 1:
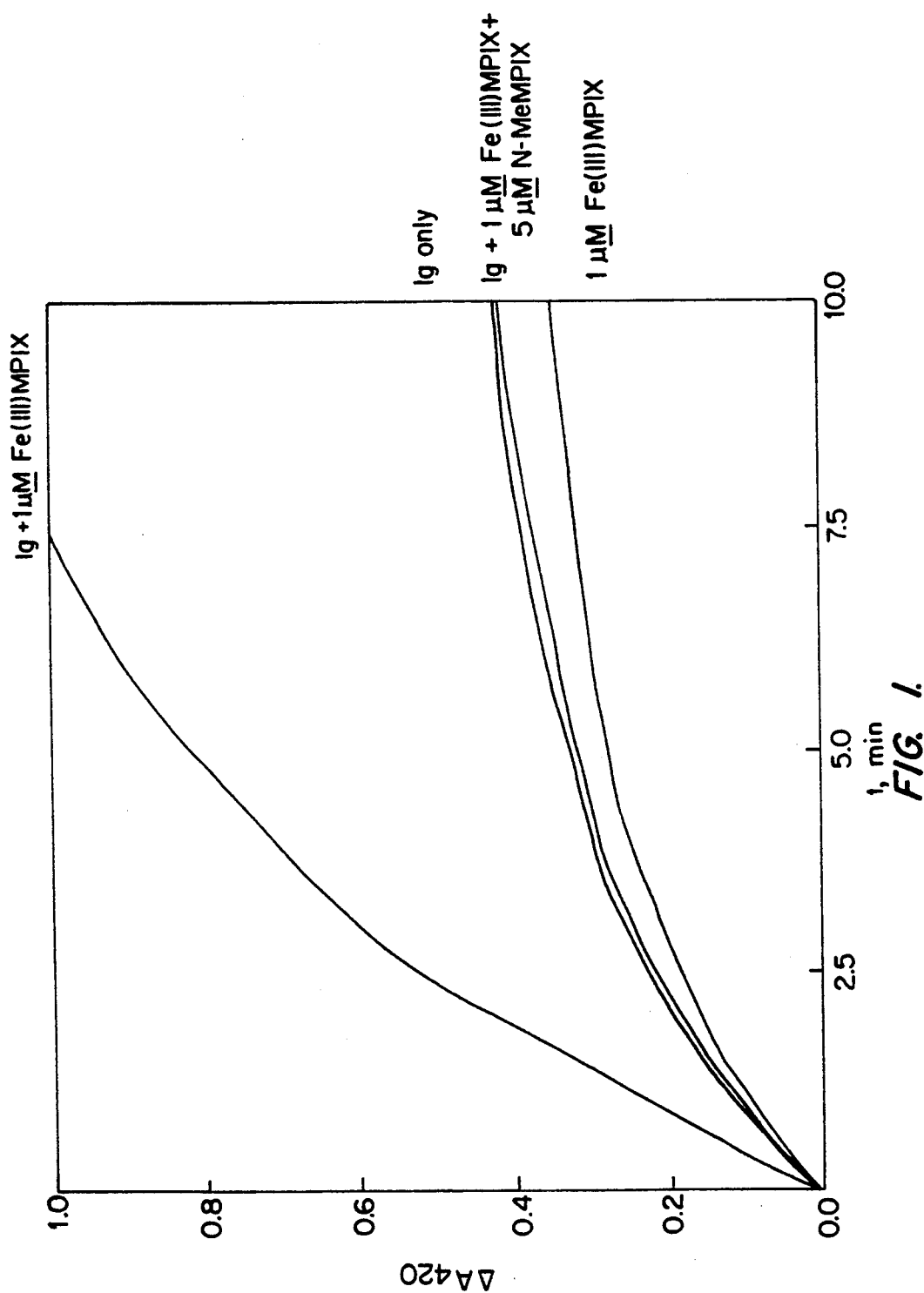
FIGS. 1, 2, 3 and 4 are depictions of experimental results obtained using various embodiments of the invention.

In the general sense, this invention is applicable to all chemical reactions, whether having a precedent in biochemistry or not, which would otherwise be rate enhanced by an enzyme-cofactor complex. The substrate upon which the enzyme-cofactor complex, or in the case of the present invention the antibody-cofactor complex, would act may be either a single reactant or a combination of reactants. The antigen binding site includes a region complementary to the cofactor. The site may thus be complementary to the cofactor only, to a particular form if the cofactor is capable of assuming more than one form, or to a complex of the substrate and cofactor. In either case, the binding site will be complementary to the cofactor or complex in a conformation which promotes the action of the cofactor on the substrate and hence the desired chemical reaction. In preferred embodiments, the antigen binding site is complementary to a complex of the cofactor and the substrate, and in further preferred embodiments, the complex is a transition state complex or a high-energy complex in general along the reaction coordinate.

Examples of classes of reactions contemplated as being within the scope of the invention are given below. As will be readily apparent to those skilled in the art, these classes overlap in certain cases, and are therefore not intended to be mutually exclusive. Following the listing by reaction class are descriptions of certain groups of reactions for which distinct classes of cofactors are effective.

Examples of specific reactions and the preparation of specific haptens appearing below are offered strictly for purposes of illustration, and are intended neither to limit nor define the invention in any manner.

In these descriptions, the term "nicotinamide-based compounds" refers to nicotinamide adenine dinucleoside (NAD), 1,2-dihydro-NAD, 1,4-dihydro-NAD, 1,6-dihydro-NAD and NAD phosphate (NADP). The term "flavin-based compounds" refers to flavin, 1,5-dihydroflavin, riboflavin, flavin mononucleotide and flavin adenine dinucleotide. The term "pterin-based compounds" refers to pterin, 7,8-dihydrobiopterin, 5,6,7,8-tetrahydrobiopterin, quinoid dihydropterin and pterin hydroperoxide. The term "ferredoxin-based compounds" refers to reduced ferredoxins, oxidized ferredoxins, and metalloferredoxin complexes such as those of ferredoxin with molybdenum and iron. The term "pyridoxal-based compounds" refers to pyridoxal, pyridoxal phosphate, pyridoxamine, pyridoxamine phosphate and pyridoxol. The term "porphyrinbased compounds" refers to porphyrins, mesoporphyrins, protoporphyrins, and metallo-complexes of these compounds.

I. Redox Reactions

Examples of reactions within this class are as follows:
Oxidation:
    hydroxylation of hydrocarbons
    hydroxylation of arenes
    hydroxylation of amines
    hydroxylation of thiols
    oxidation of alcohols to carbonyl compounds
    oxidation of aldehydes to carboxylic acids
    oxidation of ketones to esters
    oxidation of thiols to disulfides, sulfones or sulfoxides oxidation of sulfides to sulfones or sulfoxides
oxidation of amines to imines
epoxidation of arenes
oxygenation of arenes
oxygenation of arenes
epoxidation of olefins
oxidative cleavages of carbon-carbon and carbon-nitrogen bonds Reduction:
reduction of carboxylic acids to aldehydes
reduction of esters to ketones
reduction of disulfides to thiols
reduction of sulfoxides or sulfones to sulfides
reduction of carbonyl compounds to hydroxyl compounds or hydrocarbons
reduction of imines to amines
stereospecific reductions of carbonyl compounds to imines
reductive cleavages Auxiliary species or cofactors useful in promoting these reactions are as follows:
nicotinamide-based compounds
flavin-based compounds
pterin-based compounds
ferredoxin-based compounds
thiamine pyrophosphate
pyridoxal-based compounds
ascorbic acid
complexes of metal ions with porphyrin-based compounds, phthalocyanine derivatives, polypyridyl ligands (e.g., bipyridyl), aminocarboxylate ligands (e.g., ethylenediamine tetraacetic acid), linear and cyclic polyamines (e.g., diethylenetriamine), heterocyclic ligands, and any other metal-chelating groups, including Schiff bases and polydentate macrocycles

II. Decarboxylation Reactions

Examples of substrates for this class are $\beta$-keto acids, $\beta$-hydroxy acids, $\alpha$-keto acids, and $\alpha$-amino acids. Examples of auxiliary species or cofactors are pyridoxal phosphate, thiamine pyrophosphate, hydroxyethyl thiamine pyrophosphate, a divalent metal ion, ferredoxin, nicotinamide adenine dinucleotide phosphate, and 1,4-dihydronicotinamide.

III. Carboxylation Reactions

Examples of substrates for this class are $\alpha$-keto acids, acyl-coenzyme A thioesters, ureas, and glutamyl residues of proteins. Examples of auxiliary species or cofactors are biotin, guanosine diphosphate, inosine diphosphate, adenosine diphosphate, $Ca^{+2}$, and 3-substituted 2-methyl-1,4-naphthoquinones.

IV. Hydrolysis Reactions

Examples of substrates for this class are polypeptides, carboxylic acid esters, phosphate monoesters and phosphodiesters. Examples of auxiliary species or cofactors are cations of divalent metals such as Zn(II), Co(II), Ni(II), Mg(II), Mn(II), Fe(II), and Ca(II), and coordination complexes of such divalent metals with hydrolysis-promoting ligands. Examples of hydrolysis-promoting ligands are pyridine-2,6-dicarboxylic acid, pyridine carboxaldoxime, bipyridine, phenanthroline, ethylenediamine, triethylene tetramine, and ethylenediamine diacetic acid, and congeners and derivatives thereof, as well as porphyrin-based compounds, phthalocyanine derivatives, polypyridyl ligands, aminocarboxylate ligands, linear and cyclic polyamines, and heterocyclic ligands. Antibodies for polypeptide substrates include those which are specific for peptide linkages at the amino terminus or the carboxy terminus of a protein, and thus function as exopeptidases, as well as those which are specific for an internal bond in the protein, and thus function as endopeptidases.

V. Phosphorylation Reactions

Examples of substrates for this class are alcohols, nucleoside phosphates, amines, carboxylate-containing compounds, enolate-containing compounds, and serine residue. Examples of auxiliary species or cofactors are divalent metal cations and complexes of divalent metals with purine and pyrimidine nucleoside triphosphates. Preferred among these are $Mg^{+2}$-adenosine triphosphate, $Mg^{+2}$-guanidine triphosphate, $Mg^{+2}$-uridine triphosphate, $Mg^{+2}$-cytidine triphosphate, $Mn^{+2}$-adenosine triphosphate, $Mn^{+2}$-guanidine triphosphate, $Mn^{+2}$-uridine triphosphate and $Mn^{+2}$-cytidine triphosphate.

VI. Condensation Reactions

Examples of reactions within this class are aldol condensations, Claisen condensations and oxidative condensations. Examples of substrates are $\alpha$-keto acids, aldehydes, ketones, acylthioesters and glycines. Examples of auxiliary species or cofactors are inorganic bases, divalent metal cations, thiamine pyrophosphate, pyridoxal phosphate, and other pyridoxal-based compounds.

VII. Elimination Reactions

Examples of substrates for water eliminations within this class are monohydroxy compounds, dihydroxy compounds and polyhydroxy compounds, including those with vicinal hydroxyl groups as well as those with nonvicinal hydroxyl groups. Auxiliary species or cofactors for this group include divalent metals, divalent metal cations, coenzyme $B_{12}$, nicotinamide adenine dinucleotide, pyridoxamine phosphate, and inorganic bases.

Examples of substrates for ammonia eliminations are primary amines, secondary amines, and $\alpha$-amino acids. Auxiliary species or cofactors for this group include pyridoxal phosphate and inorganic bases.

VIII. Isomerization Reactions

Examples of reactions within this class are 1,1-hydrogen shifts, where the substrate is a compound having an asymmetric center; 1,2-hydrogen shifts, where the substrate is an $\alpha$-hydroxy aldehyde, allylic isomerizations, and cos-trans isomerizations. Auxiliary species or cofactors are divalent metal cations, inorganic bases, coenzyme A, nicotinamide adenine dinucleotide and pyridoxal phosphate.

The following classes are grouped by cofactor type.

IX. Redox Reactions Using Flavin-type Cofactors

Redox reactions involving the use of a flavin-based compound include both oxidations and reductions, and the flavin-based compound may be any of the known flavin derivatives, selected on the basis of the specific reaction. For example, for oxidation reactions, the cofactor may be an oxidized form of a flavin-based compound. Examples of oxidation reactions which may be enhanced in this manner are those involving the oxidation of an alcohol to a carbonyl, the oxidation of a thiol to a disulfide, the oxidation of an aldehyde to a carboxylic acid, and the oxidation of an ionizable carbon acid and aromatic hydrocarbons. Conversely, for reduction reactions, the cofactor may be a reduced form of a flavin-based compound. Examples of reduction reactions are those which are the reverse of the oxidation reactions cited above. Flavin-based compounds useful in these reactions include flavin itself, 1,5-dihydroflavin, riboflavin, flavin mononucleotide and flavin adenine dinucleotide.

As an example of one embodiment of the invention, either a reduced or an oxidized form of flavin is made substantially stronger as a reducing or oxidizing agent, respectively, by using it in conjunction with an antibody having specific binding affinity for the opposite form, i.e., the oxidized or reduced form, respectively. The resulting combination is a considerably stronger reducing or oxidizing agent than the flavin-based compound itself.

Flavin is a derivative of riboflavin that functions as the prosthetic group in flavoproteins. The oxidized form is shown as Formula I below and the reduced form, also referred to as 1,5-dihydroflavin, as Formula II:

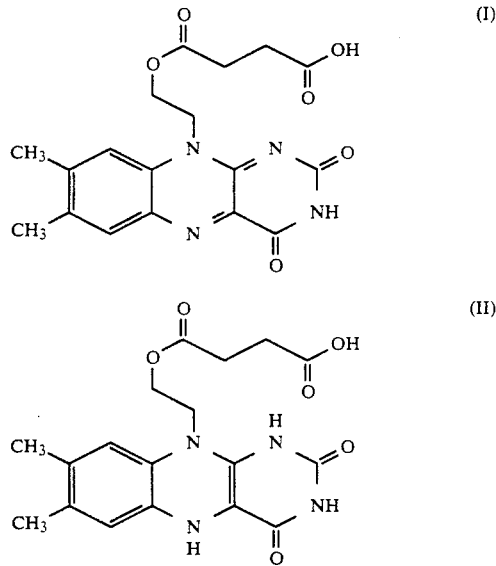

The oxidized form is useful as an oxidizing agent for oxidixable substrates in general, while the reduced form is similarly useful as a reducing agent.

Flavin and 1,5-dihydroflavin are known species, commercially available, and readily capable of preparation from natural sources in accordance with conventional techniques. Flavin may be synthesized, for example, from riboflavin, a vitamin widely distributed in nature, by periodate oxidation to give 10-(formylmethyl)riboflavin, followed by reduction (with sodium borohydride, for example) and reaction with succinic acid. The reduced form (Formula II) is readily obtained by the reduction of flavin using conventional reducing agents.

To prepare the antibody, the flavin-based compound which the antibody is to be complementary to may be used as a hapten by coupling to a carrier protein using conventional linking agents and coupling reactions. Antibodies are then generated in accordance with conventional procedures for which further description is provided below.

Once the antibodies are obtained, the complex may be formed in various ways readily apparent to those skilled in the art. Using a reduction reaction as an example, the 1,5-dihydroflavin itself may be combined directly with the antibody under conditions favoring immunological binding. As an alternative, however, the complex may be formed by combiing flavin rather than 1,5-dihydroflavin with the antibody, again under conditions favoring immunological binding, followed by subjecting the resulting complex to reducing conditions to convert the bound flavin to 1,5-dihydroflavin. Conventional reducing conditions may be used. One example is the use of anaerobic dithionite (i.e., zinc and sodium hydrosulfite).

Use of the complex described in the preceding paragraph as a reducing agent for a reducible chemical species is performed according to conventional techniques. The complex precludes the need for an enzyme, thereby providing the flavin with sufficient chemical properties of its own to promote the reaction at a commercially reasonable and cost effective rate. The reduction reaction will generally take place in aqueous solution in the presence of a buffer to maintain the pH at the desired level. While the actual pH may not be critical, satisfactory results will in most cases be achieved at neutral pH or a value close thereto.

Antibodies generated in this manner are applicable to a wide range of reductions, and thus a wide range of chemically reducible substrates, notably those susceptible to reduction by flavin or its analogs, including those which are susceptible to reduction by flavin as a cofactor in combination with an enzyme. Similarly, antibodies generated for oxidation reactions are applicable to a wide range of oxidation reactions. In the case of reductions, the reduction potential of flavin itself bound to antibody is $-341$ mV as compared with the reduction potential of flavin alone of $-206$ mV. The present invention will thus be of particular interest as applied to substrates having a reduction potential within the range of from about $-206$ mV to about $-342$ mV. Similar considerations apply for oxidation reactions.

EXAMPLE 1

This example demonstrates the reduction of the dye Safranine T with 1,5-dihydroflavin, both free and as a complex with antibody.

Flavin (Formula I above) was formed by periodate oxidation of riboflavin, followed by reduction with sodium borohydride and reaction with succinic anhydride. The product was characterized as follows:

m.p. 194°–198° C.;

UV/VIS (0.1N NaOH): $\lambda(\lg\epsilon) = 269$ (4.71), 355 (4.25), 450 nm (4.26);

$^1$NMR ([D$_6$]dimethyl sulfoxide): $\delta = 2.09$ (t, 2H, J=11 Hz), 2.23 (t, 2H, J=11 Hz), 2.35 (s, 3H), 2.42 (s, 3H), 4.37 (t, 2H), 4.80 (t, 2H), 7.83 (s, 2H), 11.35 (br. s, 1H);

FAB+-MS (high resolution): 387.1305 ($C_{18}H_{19}N_4O_6$, MH$^\oplus$).

The flavin thus produced was coupled to carrier proteins bovine serum albumin and keyhole limpet hemocyanin separately using water-soluble carbodimide according to known procedures as described in Erlanger, B. *Methods Enzymol.* 70 (1980) 85, and antibodies were generated in separate immunizations according to conventional techniques as described in Hurn, B., et. al., 70 (1980) 104. Six clones were obtained and purified from mouse ascites fluid by Protein-A chromatography and were judged homogeneous by sodium dodecyl sulfate polyacrylamide gel electrophoresis with Coomassie blue staining.

Complexes of the antibody with flavin were formed, and were stoichiometrically reduced with dithionite. Aliquots of Safranine T (whose reduction potential is $-289$ mV) at 6 mM (aqueous) were then added to an aqueous solution of the complex, which consisted of 1,5-dihydroflavin (30 $\mu$M) bound to antibody (31 $\mu$M), in 0.1M phosphate at pH 7.0 under anaerobic conditions. The progress of the reaction was monitored by The transition state will be stabilized by the antigen binding site. The antibody thereby lowers the energy barrier of the reaction, providing the flavin with an enhanced reactivity in the absence of an enzyme. Generation of the antibody is achieved by the use of the flavin-substrate complex, or a stable analog thereof with a similar steric and electric conformation, as a hapten.

For example, generation of an antibody to hapten (III) below will create a binding site for an oxidized flavin cofactor and the corresponding amino acid. The resulting antibody will then catalyze the oxidation of the amino acid to the keto acid.

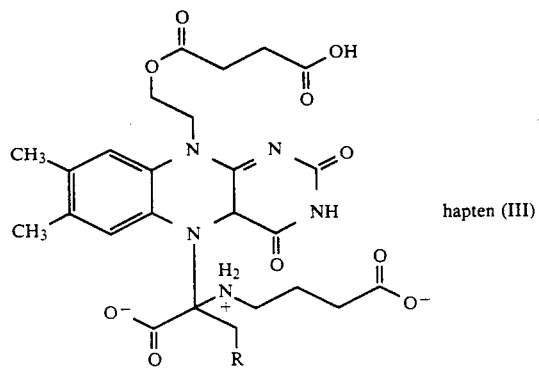

hapten (III)

Reaction:

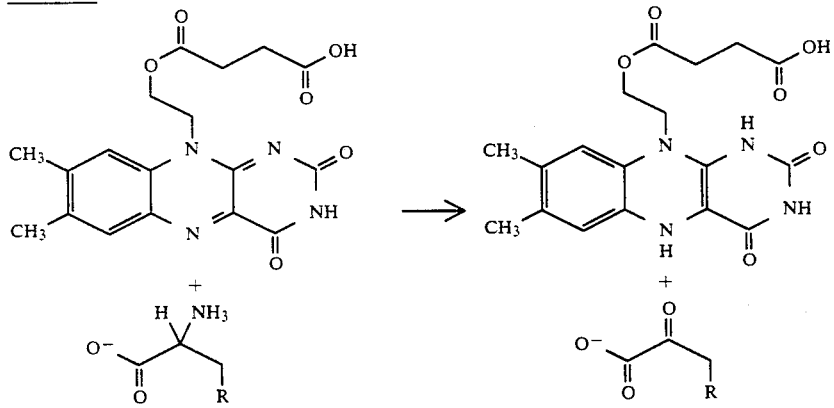

monitoring the oxidation of the 1,5-dihydroflavin-antibody complex as indicated by increases in absorbance at 375 and 458 nm, it having previously been determined that the UV spectrum of the flavin-antibody complex displays a 15-nm bathochromic shift (443 to 458 nm) and a 375-nm maximum, indicating association with the aromatic amino acid side chains in the antibody-combining site. By monitoring the absorbance in this manner, it was determined that the reaction proceeded rapidly. After the addition of each aliquot of Safranine T, no absorption due to oxidized Safranine T (510 nm) was observed, indicating that the antibody-bound 1,5-dihydroflavin had indeed reduced the Safranine T.

The experiment was then repeated without the antibody present, i.e., only free 1,5-dihydroflavin and oxidized Safranine T. No reduction of the Safranine T was observed.

The present invention also extends to antibodies which incorporate a substrate binding site in addition to the flavin binding site, as well as the complexes which they form. The binding site will thus be complementary to a flavin-transition state complex which will be readily convertible to the reduced or oxidized product.

X. Reactions Using Metalloporphyrins as Cofactors

Oxidation-reduction reactions using metalloporphyrins as cofactors involve the use of a porphyrin group to bind the metal ion in such a manner as to cause the metal ion to bind and activate oxygen for oxidation of alkanes or alkenes. An external oxidant such as $H_2O_2$ is needed as the electron sink.

Prime examples of porphyrins are heme prosthetic groups, which are present on proteins existing in all free-living organisms. These heme-containing proteins play diverse roles. Hemoglobin and myoglobin, for example, reversibly bind dioxygen for transport. Cytochromes transfer electrons one at a time in membranous respiratory chains. Catalases and peroxidases reduce peroxides. Further heme-containing proteins are part of multienzyme systems involved in hydroxylations of steroid hormones, steroidal bile acids, fatty acids, xenobiotic hydrocarbons (for detoxification) and camphor, in which these proteins act as a terminal component.

In almost all instances, the prosthetic group, which is tightly and sometimes covalently bound to apoenzyme, involves an iron atom, Fe(III) or Fe(II), coordinated to a macrocyclic tetrapyrrole ring (protoporphyrin IX). The pyrrole nitrogens provide four ligands to the iron in equatorial positions, leaving the two axial positions available for other ligands. The bottom axial position is generally filled by a ligand from the apoprotein. The top axial position may be filled by a ligand from the protein, $H_2O$, $O_2$ or, adventitiously, by CO or $CO_2$ (serving as inactivators). In hemoglobin and myoglobin, the bottom axial ligands are imidazole nitrogens of histidine residues. In the cytochrome $P_{450}$, the bottom axial ligand is believed to be a cysteinyl sulfur, which is believed to affect the coordinated $O_2$ at the top axial position to polarize the O—O bond sufficiently to prepare it for fission.

In one example of applying the present invention to reactions involving metalloporphyrins, antibodies are generated to Rh-CO mesoporphyrin. These antibodies have a metal binding site as well as a binding site for the oxygen ligand. When reconstituted with Fe(III) or Mn(II) mesoporphyrin, the antibody will have oxidase activity. The antibody will serve to prevent dimerization of the metalloporphyrin in solution and will provide an axial ligand to the metal via antibody-hapten complementarity.

The metalloporphyrin hapten may be further modified for specific types of reactions. Generation of a third ligand (or addition of an exogenous thiol such as mercaptoethanol) on the hapten, for example, will provide an antibody with oxidative activity in the presence of an external electron sink such as $H_2O_2$. Generation of an imidazole group on the hapten will provide an antibody with reversible $O_2$ binding activity. Derivatization of the porphyrin with alkyl groups (N-phenyl or N-n-alkyl) will elicit antibody combining sites that not only bind metalloporphyrins but that also have a substrate (aryl or alkyl) binding site. The juxtaposition of the substrate and metalloporphyrin will allow stereospecific oxidation reactions such as hydroxylation of alkanes or epoxidation of olefins.

Specific examples of reactions involving metalloporphyrins which will be catalyzed by appropriately elicited antibodies in accordance with this invention are camphor oxidation, the oxidation of cholesterol to aldosterone, the oxidation of cholesterol to hydrocortisone, and the epoxidation of benzopyrene and phenol. Other examples will be readily apparent to those skilled in the art from the description above.

EXAMPLE 2

N-Methyl mesoporphyrin (NMMP), a commercially available species obtained from Porphyrin Products, Logan, Utah, having the formula

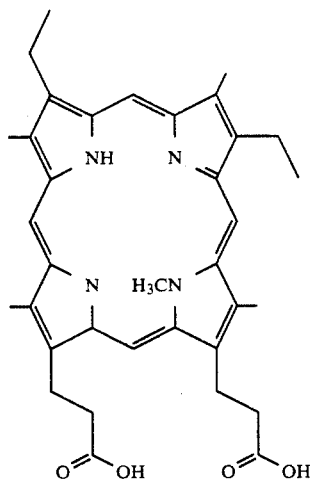

was conjugated to a carrier protein by treatment of the NMMP with N-hydroxysuccinimide (NHS) and dicyclohexylcarbodiimide, followed by addition of the resulting NHS ester to a solution of the protein. Monoclonal antibodies were elicited in accordance with conventional procedures known to those skilled in the art, and purified by Protein A affinity chromatography.

Two of three antibodies obtained catalyzed the chelation of a variety of metal ions by mesoporphyrin IX:

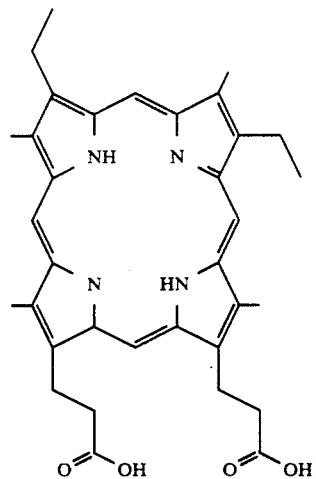

Further study of the faster of the two antibodies 7G12-A10-G1-A12, revealed that the catalytic ability of this antibody was inhibited by various metalloporphyrins in addition to the hapten. Among the metalloporphyrins tested, those most effective as inhibitors were iron(III)-mesoporphyrin, as shown below:

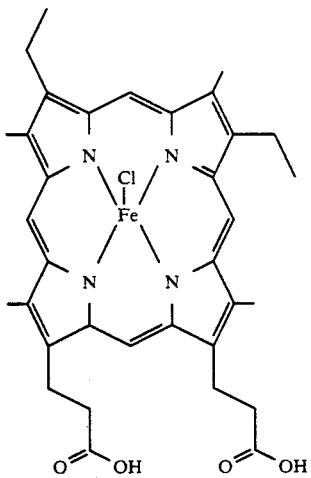

and manganese(III)mesoporphyrin. The inhibition constant ($K_i$) for the iron(III)mesoporphyrin was less than 10 nM. The term "mesoporphyrin" is used here as an abbreviation for the more complete term "mesoporphyrin IX," and the abbreviations "MP" and "MPIX" are used interchangeably to refer to this species. Thus, "Fe(III)-mesoporphyrin," "iron(III)mesoporphyrin" and "Fe(III)MPIX" are equivalent, and "N-methyl nesoporphyrin," "NMMP" and "N-MeMPIX" and likewise equivalent.

In one experiment, the antibody was used for oxidation of pyrogallol as determined spectrometrically by monitoring pyrogallol disappearance. The reaction was as follows:

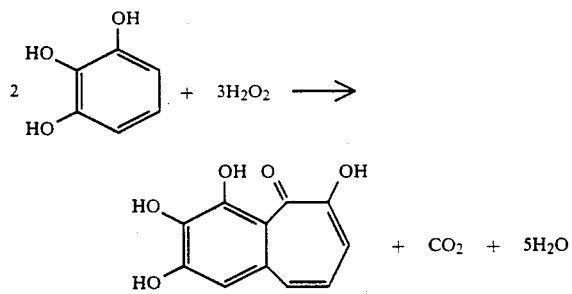

The product has a maximum absorption at 420 nm. To demonstrate the effectiveness of the isolated antibody, the reaction was conducted in the presence of the following individually:
(a) 1 μM Fe(III)-mesoporphyrin only;
(b) the antibody only;
(c) the antibody plus 1 μM Fe(III)-mesoporphyrin and 5 μM NMMP; and
(d) the antibody plus 1 μM Fe(III)-mesoporphyrin only.
The absorption at 420 nm was monitored over time in each case, and the results are shown in FIG. 1. What the results indicate is that the reaction rate achieved using the combination of the antibody and the Fe(III)-mesoporphyrin far exceeded the reaction rates achieved with either the antibody or the Fe(III)-mesoporphyrin alone, and also far exceeded that achieved when the NMMP was present. The NMMP thus blocked the antigen binding site of the antibody, destroying the catalytic effect of the antibody.

In further experiments, this antibody was used in the presence of $H_2O_2$ to catalyze the oxidation of the following group of typical chromogenic peroxidase substrates:

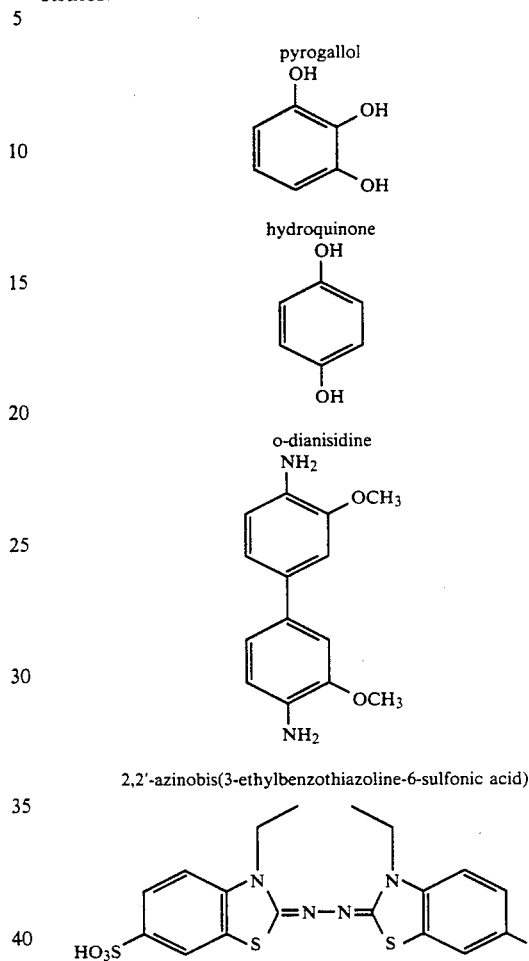

Reaction mixtures contained 1 mM reducing substrate, 5 mM hydrogen peroxide, 0.5 mM Fe(III)mesoporphyrin chloride (mesohemin), 0.5% w/v Triton X-100, 4% v/v dimethyl sulfoxide (DMSO), and 90 mM tris acetate, pH 8.0, and were incubated at 10° C. Antibody samples contained 0.2 mg/mL (1.3 μM) protein.

Figure 2:
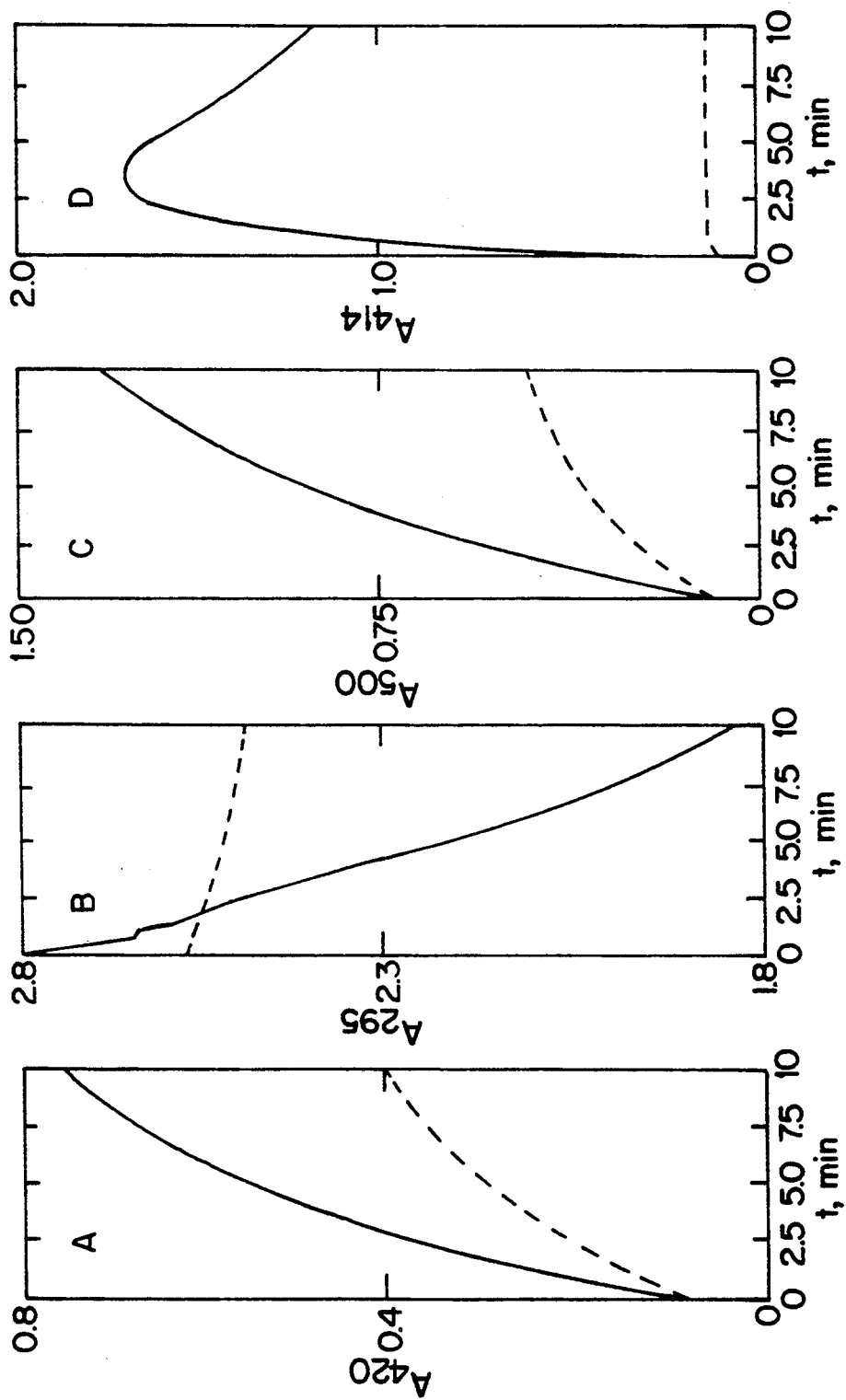

Each of the reactions was monitored at a selected wavelength with a Kontron Instruments Uvikon 860 ultraviolet-visible spectrophotometer, and the results are shown in FIG. 2, where the solid line in each case represents the reaction occurring in the presence of the antibody-mesohemin complex and the dashed line represents the reaction in the presence of the mesohemin alone, without the antibody. The monitored wavelength and $\Delta\epsilon$ value for each reaction, and the plot in FIG. 2 showing the corresponding absorption curves for each comparison are as follows:
pyrogallol: $\lambda=420$ nm; $\Delta\epsilon=3200 M^{-1}$; plot A
hydroquinone: $\lambda=295$ nm; $\Delta\epsilon=-2500 M^{-1}$; plot B
o-dianisidine: $\lambda=500$ nm; $\Delta\epsilon=7500 M^{-1}$; plot C
2,2'-azinobis(3-ethylbenzothiazoline-6-sulfonic acid):
$\lambda=414$ nm; $\Delta\epsilon=36,000 M^{-1}$; plot D
In all cases, peroxidation catalyzed by the antibody-mesohemin complex was faster than oxidation in the presence of mesohemin alone (note that the second reaction has a negative $\Delta\epsilon$).

Further tests yielded the following observations. First, addition of the hapten in a stoichiometric amount (relative to antibody binding sites) completely blocked antibody catalysis in each reaction, and the antibody alone had no peroxidase activity in any of the reactions. Inhibition by hapten and a requirement for added cofactor confirms that the catalyst is in fact the antibody-mesohemin complex and not an enzyme impurity in the antibody preparation. Second, tests performed with antibody-Mn(III)mesoporphyrin complex in place of antibody-mesohemin complex indicated no peroxidase activity. Third, the other two antibodies specific for the hapten did not form complexes with peroxidase activity.

A further observation was that peroxidation of the two phenolic substrates, pyrogallol and hydroquinone, by free mesohemin was completely suppressed by the presence of added Triton X-100 or Tween 20 (added to prevent hemin dimerization). In contrast, peroxidation of o-dianisidine by free mesohemin was slightly stimulated by the added detergent. Note that the peroxidation of o-dianisidine was the only one of the four shown which was catalyzed by free mesohemin. The addition of detergent had no effect on oxidation of 2,2'-azinobis(3-ethylbenzothiazoline-6-sulfonic acid) in the presence of free mesohemin, nor did it have an effect on any of the antibody-catalyzed peroxidations.

Figure 3:
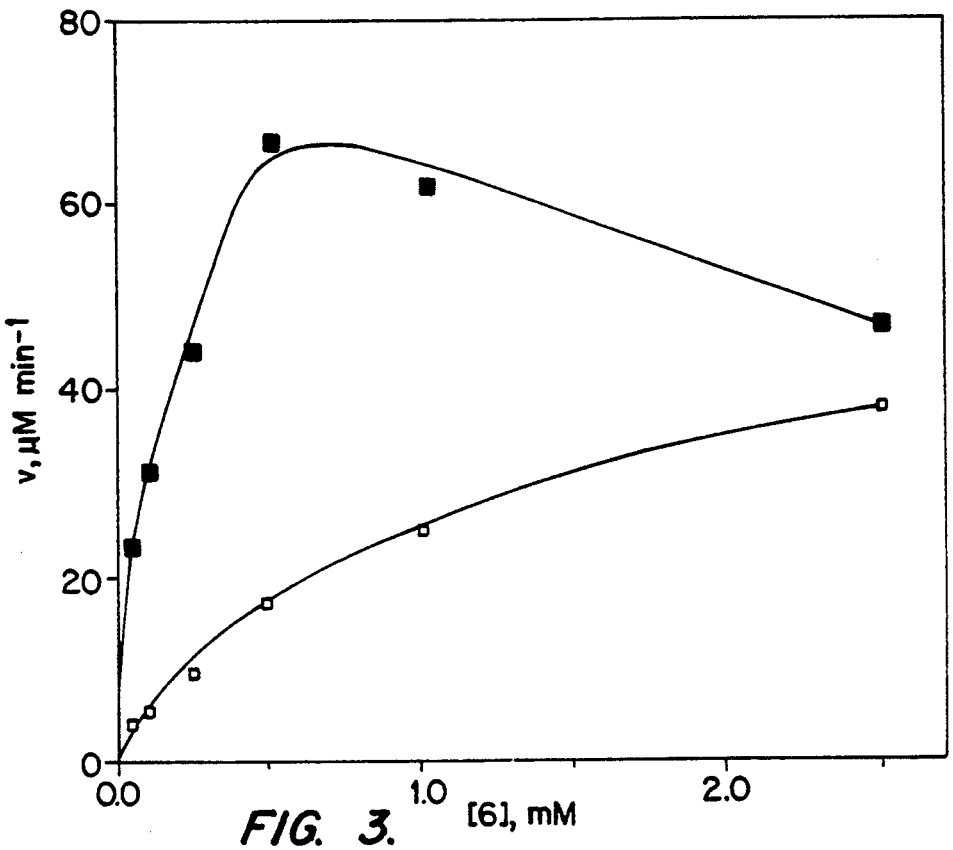

The rate of o-dianisidine oxidation was examined at several o-dianisidine concentrations, ranging from 0.05 mM to 2.5 mM, using 10 mM $H_2O_2$ in each case and other reaction conditions as described above. The initial rate of peroxidation v is shown in FIG. 3 as a function of o-dianisidine concentration for both reactions catalyzed by mesohemin alone (open squares) and reactions catalyzed by the antibody-mesohemin complex (filled squares). The plot shows that the catalysis by the complex reaches a maximum at approximately 0.5 mM o-dianisidine, possibly due to competition for the porphyrin binding site by the aromatic substrate at higher concentrations. While at first blush this may suggest binding of o-dianisidine itself to the antibody with a resulting catalytic effect, the presence of a specific binding site for o-dianisidine is unlikely due to the wide range of substrates capable of being reduced by this system.

Figure 4:
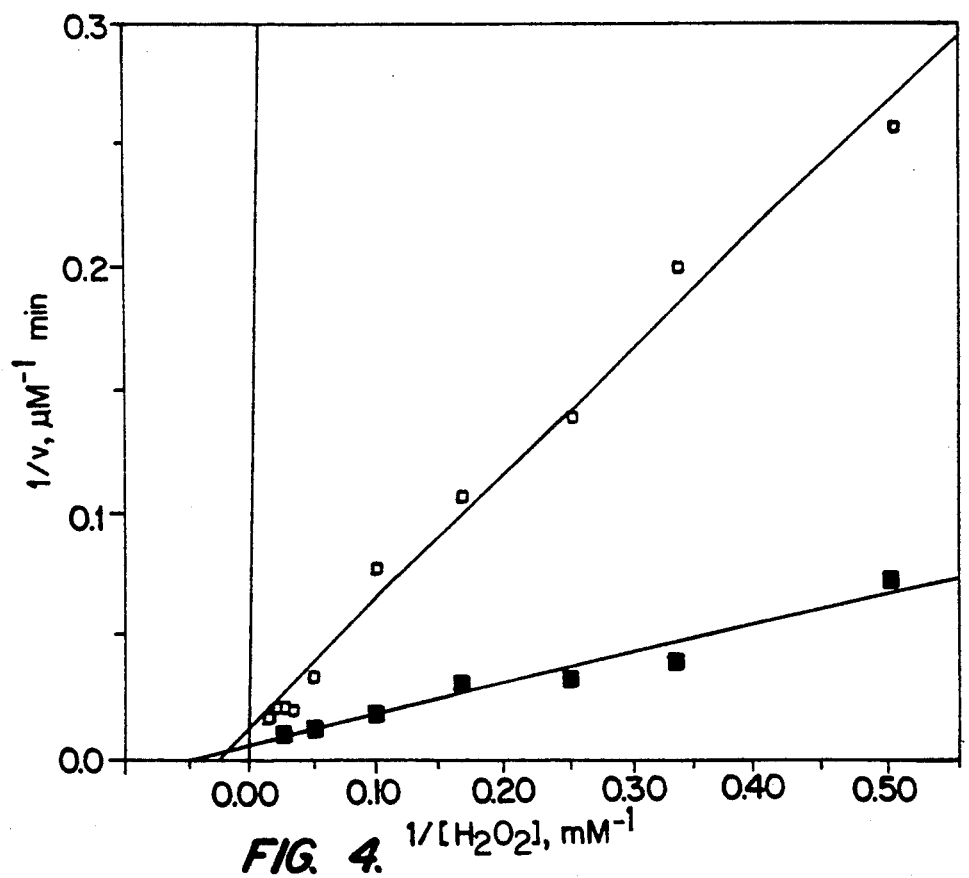

Saturation kinetics for the o-dianisidine peroxidation reaction were determined at an o-dianisidine concentration of 0.6 mM, with the remaining reaction conditions as described above. Lineweaver-Burk plots are shown in FIG. 4 for both free mesohemin (open squares) and antibody-mesohemin complex (filled squares) as a function of $H_2O_2$ concentrations. The rates shown are based on an estimated molar extinction coefficient ($\epsilon$) of 7500 for oxidized o-dianisidine. (Note that since oxidation of o-dianisidine produces a variety of products, variation of reaction conditions such as pH will cause some variation in the composition of product and therefore in the exact value of $\epsilon$. The given value is taken from a commercial assay for peroxidase activity performed in acetate buffer at pH 5.1 (Sigma Chemical Co.) and thus may not be absolutely correct for the reaction conditions used here. Nevertheless, for the free mesohemin, $K_m=43$ mM, $K_{cat}=166$ min$^{-1}$, and $K_{cat}/K_m=64$ $M^{-1}s^{-1}$; for the complex, $K_m=24$ mM, $k_{cat}=394$ min$^{-1}$, and $K_{cat}/K_m=274$ m$^{-1}$s$^{-1}$. The $K_{cat}/K_m$ value for 2,2'-azinobis(3-ethylbenzothiazoline-6-sulfonic acid) was comparable at 233 $M^{-1}s^{-1}$, and the $K_{cat}/K_m$ value for pyrogallol was likewise comparable at 122 $M^{-1}s^{-1}$. These $K_{cat}/K_m$ values compare with values of approximately $10^7$ $M^{-1}s^{-1}$ for peroxidases, which are the most efficient enzymes known. Note again that peroxidation of these substrates was not catalyzed by free mesohemin. The peroxidation of substrates o-dianisidine and 2,2'-azinobis(3-ethylbenzothiazoline-6-sulfonic acid) by a non-peroxidative heme protein, sperm whale myoglobin (Fluka), was barely detectable under reaction identical conditions.

XI. Additional Reactions Involving Transition Metals as Cofactors

This class includes a variety of subclasses, such as reactions in which transition metal ions, when present as a complex with enzymes, act as reduction-oxidation centers, or reactions in which the metal cofactor acts as an electrophile to facilitate amide, ester and phosphodiester hydrolysis or reduction of carbonyls or imines. Specifically, the metal ions act as Lewis acids polarizing the carbonyl carbon and thereby increasing its attraction to the nucleophile. The metal ions can also act to modulate the $pK_a$ of a bound ligand such as a water molecule, increasing its nucleophilicity for attack on an amide, ester or phosphodiester linkage.

In each of these reactions and others which will be apparent to those skilled in the art, enzymes are known which stabilize the transition state complex of the metal ion and the substrate, thereby promoting the progress of the reaction. Examples are the $Zn^{+2}$ ion in combination with carboxypeptidase A (nucleophilic attack on a carbonyl) and in combination with carbonic anhydrase to facilitate conversion of $CO_2$ to carbonate.

Examples of reactions in which the transition metal ions act as redox-active centers are oxidation or reduction reactions normally catalyzed by enzymes. Specific examples are $Fe^{2+/3+}$ and $Cu^{1+/2+}$ ions, typically used in context hemoglobin or hemocyanin for oxygen transport, or with cytochromes for electron transport, and $Fe^{2+/4+}$ in conjunction with $P_{450}$ for steroid oxidation or isopenicillin N synthetase for the synthesis of penicillins and cephalosporins.

In the present invention, an antibody serves to lower the free energy of activation for reaction by bringing together the substrate and cofactor in a reactive conformation. The antibody combining site may also enforce stereochemical control on the course of the reaction. The antibody is generated by an appropriate hapten which will generally be a hybrid or conjugated structure containing moieties analogous in steric and electronic conformation to the transition metal ion-ligand complex and the substrate. The arrangement of these moieties in the hybrid structure will closely approximate the transition metal ion and substrate in the relative orientation and spacing needed for the reaction to proceed.

The example of an antibody substituting for isopenicillin N synthetase (IPNS) may be elaborated as follows.

IPNS is known to catalyze the oxidative condensation of δ-(L-α-aminoadipyl)-L-cysteinyl-D-valine to isopenicillin N, a central reaction in the biosynthetic pathway to clinically important penicillins and cephalosporins. The oxidative condensation is believed to occur through the formation of a highly reactive β-lactam-iron oxene transition state which mediates ring closure with retention of stereochemistry.

The antibody substituting for IPNS will act to bind an oxidizing metal polypyridyl complex (e.g., a $Cu^{2+}$ or $Fe^{3+}$ bipyridyl complex) and stabilize the analogous transition state for oxidation of the acyclic β-lactam substrate. The antibody will therefore favor the formation of the polypyridyl-ligated metal and the positioning of this species in relation to the substrate in a particular orientation which favors joining of the carbon and sulfur atoms on the substrate to close the ring in a stereospecific fashion. To perform the reaction, the antibody is thus combined with the substrate, the metal ion, the pyridyl ligand, oxygen, and a sacrificial electron donor. The result is the desired ring closure.

The redox-active metal used in this procedure may be any metal known to be active in such reactions. Examples are copper, iron, cobalt and ruthenium. The sacrificial electron donor may likewise be any of the wide variety of known species effective for this type of function. A prime example is ascorbate. Other examples are triethylamine, triethanolamine, water, ethylenediamine tetraacetic acid, and an electrochemical electrode. Suitable pyridyl ligands include 2,2'-bipyridine and the analogous terpyridine. The ring-forming reaction itself may be any such reaction involving the formation of a carbon-sulfur bond, preferably from a methyl group (optionally substituted) and a thiol group, respectively. The ring thus formed may range from a five-membered ring upward, including seven- and eight-membered rings, preferably five- to ten-membered rings.

The antibody will contain in its antibody-binding site a region complementary to the polypyridyl-ligated metal ion, which is preferably a bipyridyl-ligated metal ion. In preferred embodiments, the antigen binding site will be complementary to a transition state complex or high energy complex of the polypyridyl-ligated metal ion and the substrate, the complex being one which readily degrades to the ring-containing product.

Such antibodies may be elicited against haptens in the form of exchange-inert complexes which approximate the transition states sought to be stabilized. Examples of metals which can be used in bipyridyl complexes are cobalt and rhodium. The hapten may also approximate the transition state for ring closure by substituting a sulfur atom for the carbon atom which takes part in the closure in the actual substrate.

EXAMPLE 3A

This example illustrates the use of a hapten to elicit antibodies used for the ring closure of compound IV:

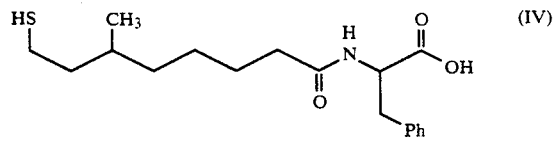

(IV)

to the ring product, compound V:

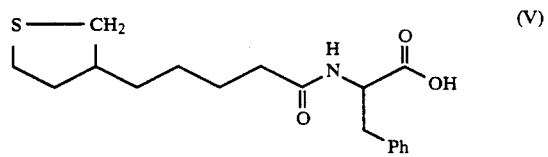

(V)

A hapten is formed as follows.

Bis-bipyridyl-dichlororhodium chloride is reacted with dihydrolipoic acid in the presence of triethylamine and ethanol at elevated temperature, followed first by treatment with dicyclohexylcarbodiimide, phenylalanine methyl ester, 1-hydroxybenzotriazole and dimethylformamide, and then by treatment with KOH and water at elevated temperature, to yield the following, compound VI:

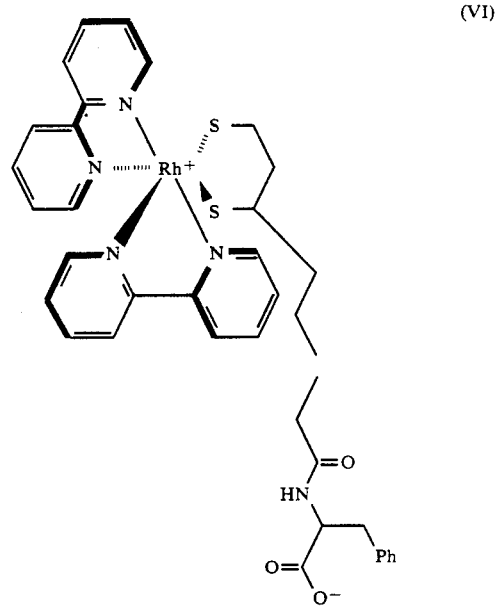

(VI)

This hapten is then conjugated to keyhole limpet hemocyanin or bovine serum albumin by a $(CH_3)_2N(CH_2)_3N=C=NC_2H_5 \cdot HCl$ coupling or other conventional coupling.

EXAMPLE 3B

This example illustrates the use of a hapten to elicit antibodies used for a ring closure reaction to produce the monocyclic Penicillin analogue (Compound VIII) by the following reaction:

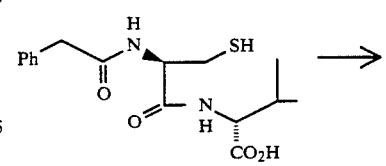

(VII)

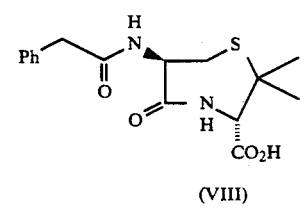

(VIII)

A hapten to elicit the appropriate antibody is formed as follows.

N,N'-bisphenylacetyl-L-cystine and bis-D-penicillamine are reacted in the presence of 2-ethoxy-1-ethoxycarbonyl-1,2-dihydroquinoline and tetrahydrofuran, followed first by treatment with Zn and HCl in methanol, then iodine in methanol to obtain phenylacetyl-L-cysteinyl-D-penicillamine, which is then treated with ω-aminovaleric carboxamidomethyl ester, dicyclohexylcarbodiimide, 1-hydroxybenzotriazole and triethylamine in dimethyl formamide, followed by (i) reduction with Zn and HCl in methanol, (ii) treatment with bis-bipyridyl-dichlororhodium chloride in the presence of triethylamine and acetonitrile at elevated temperature, and (iii) hydrolysis with sodium carbonate in water, to yield the following hapten, Compound IX:

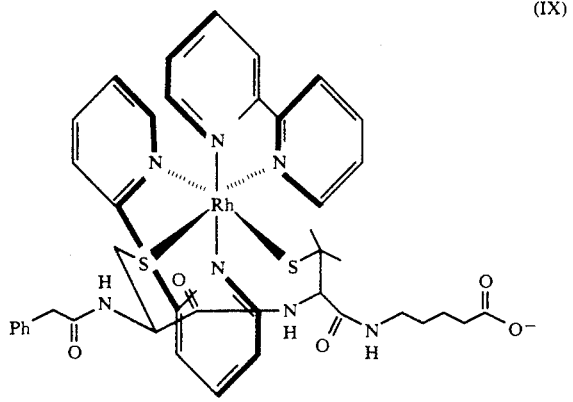

This hapten is conjugated to keyhole limpet hemocyanin or bovine serum albumin by a $(CH_3)_2N(CH_2)_3N=C=NC_2H_5 \cdot HCl$ coupling or other conventional coupling.

A further subclass of reactions within this group are those involving a labile metal cofactor system. This covers a wide variety of reactions. Notable examples are ester and amide hydrolyses, oxidative peptide cleavages, reduction of carbonyl compounds, and peptide ligations.

Application of the invention to this class may be understood by examining the example of peptide hydrolyses in detail. In accordance with the invention, an antibody is used to mimic the action of exopeptidases such as carboxypeptidase A and carboxypeptidase B, endopeptidases, or metalloenzymes in general which maintain the metal in a labile state so that it can promote the hydrolysis in a catalytic rather than a stoichiometric manner. The metal ion is used in combination with a ligand which forms a complex with the metal ion, preferably a chelate complex, the complex being one which provides the metal ion with the appropriate coordination geometry. The reaction system thus consists of a combination of the substrate, the electrophilic metal, the ligand, water, and an appropriately elicited antibody.

Metals suitable for use in these systems are electrophilic metals capable of forming a transition state complex with the substrate which will lead to the desired product. Selection of the optimum metal in each case will depend on the particular reaction sought to be performed, the appropriate choice being readily apparent to those skilled in the art. Examples are Ni(II), Zn(II) and Co(III). For peptide hydrolyses, Co(III) is particularly preferred.

The ligand may vary as well, as may the number of ligand molecules used per metal atom in the formation of the ligand-metal complex. Examples are pyridine-2,6-dicarboxylic acid, pyridine carboxaldoxime, ethylenediamine, triethylene tetramine, and ethylenediamine diacetic acid. The optimum ligand will depend on the particular reaction and will be apparent to those skilled in the art. Most of these ligands form complexes with the metal ions in stoichiometric ratios of 1:1, while others, notably ethylenediamine, are frequently used in 2:1 or 3:1 (ligand:metal) ratios.

The antigen binding site in this class of reactions will stabilize a transition state complex of the metal, ligand and substrate which upon the action of a water molecule leads to the desired bond cleavage in the substrate. Unlike the transition state complex, the cleavage products lack the close fit at the antigen binding site, and dissociation occurs, leaving the antibody available for action upon further starting material.

In peptide hydrolysis reactions, the transition state, shown below as Compound X, will include a five-membered heterocyclic ring formed by coordinating the metal ion with both the carbonyl oxygen atom and the amino nitrogen atom in a single amino acid unit:

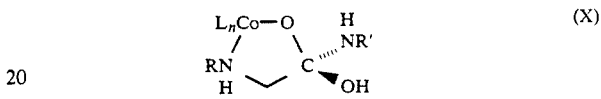

where L denotes the ligand.

To elicit antibodies complementary to the transition state, a hapten in the form of a stable analog is used, since the transition state itself is unstable. As in the other reaction classes, the analog will be one which approximates the steric and electronic character of the transition state. Examples of suitable analogs for the above transition state are the diamine, sulfoximine and sulfodiimine, shown as Compounds XI, XII and XIII below:

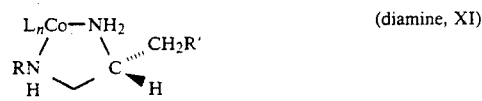

EXAMPLE 3C

This example illustrates the application of the above principle to the cleavage of a peptide bond located close to an amino terminus of a polypeptide substrate, shown below as Compound XIV. The reaction is as follows (with two examples for the R group):

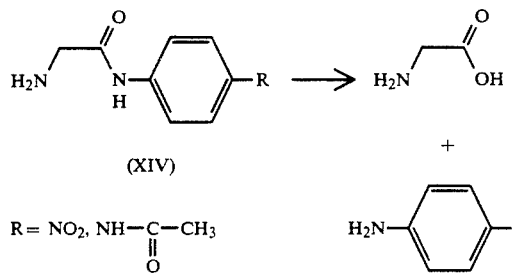

The reaction is to be conducted in the presence of water, a metal ion, and ethylenediamine diacetic acid, with an antibody elicited from a hapten-carrier protein conjugate using a diamine transition state analog as the hapten, shown below as Compound XV:

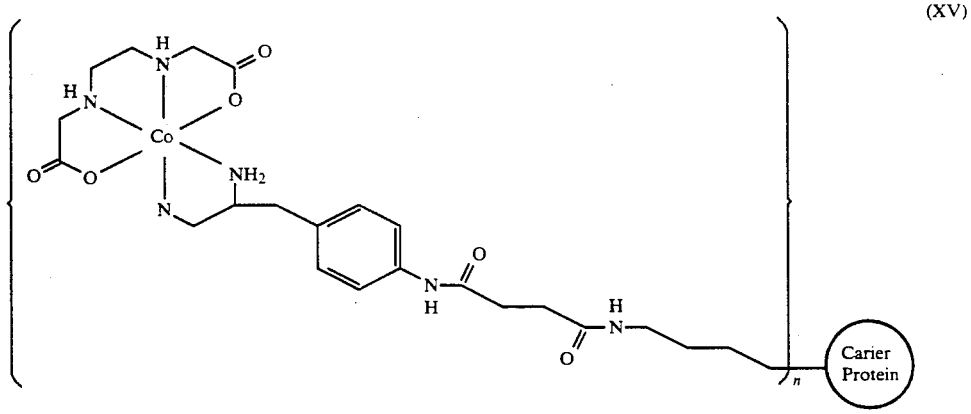

The hapten is synthesized from 3-phenyl-1-propylene by treatment with bromine followed by sodium azide and dimethylformamide to yield 3-phenyl-1,2-diazidopropane, which is then treated with copper nitrate, perfluoroacetic anhydride and chloroform to yield the p-nitro analog. The latter is then treated with triphenylphosphine and water in tetrahydrofuran to convert the azido groups to amino groups, followed by treatment first with di-t-butoxycarbonic anhydride to block both amines. The nitro group is then reduced with hydrogen gas over palladium on carbon. The latter is then treated first with succinic anhydride and dimethylaminopyridine in dimethylformamide, then with trifluoroacetic acid in methylene chloride to yield the carboxylic acid XVI:

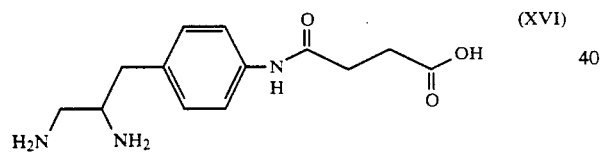

A cobalt coordination complex is then formed by reacting $Co(II)Cl_2 \cdot 6H_2O$ with $KHCO_3$ and $H_2O_2$, followed by ethylenediamine diacetic acid at 50° C., the complex XVII having the formula:

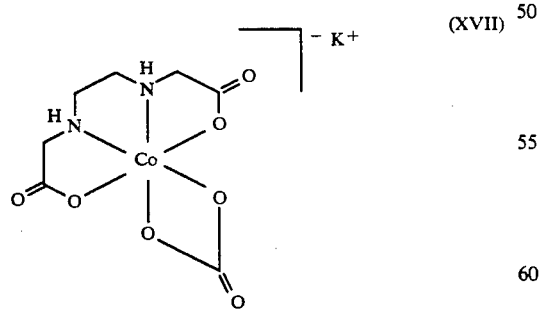

This coordination complex is then treated first with nitric acid and water, then with the above carboxylic acid in aqueous sodium hydroxide (at pH 8 to 9) at 70° C. for two hours. This produces 60% yield consisting of a 2:1 mixture of the desired hapten and an alternative isomer of this hapten. The hapten is then conjugated to a carrier protein in accordance with well known methods described elsewhere in this specification.

Application of the above principle to the cleavage of internal amide bonds proceeds in an analogous manner. The antibody in such reactions functions as an endopeptidase rather than an endopeptidase. An example of such a cleavage on a compound XVIII is as follows:

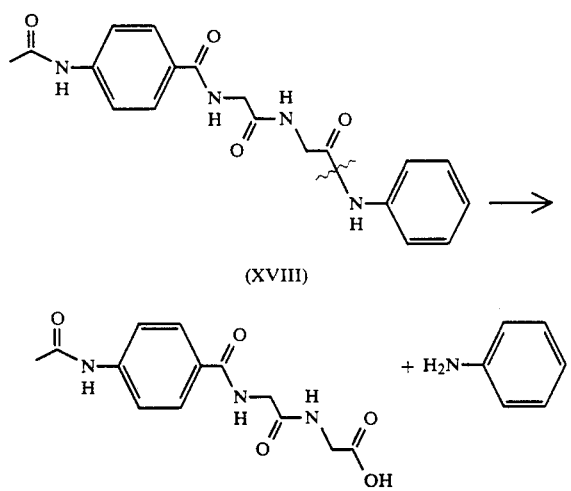

The antibody may be one which is elicited against the following hapten conjugate (Compound XIX):

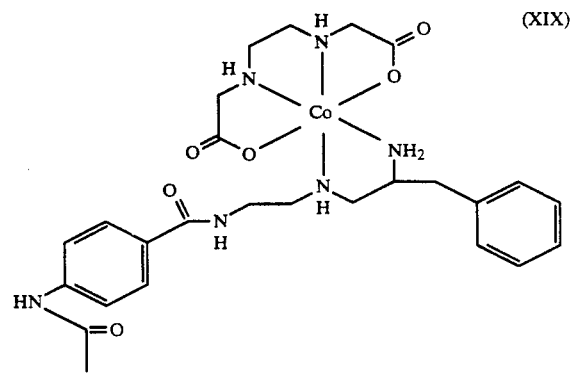

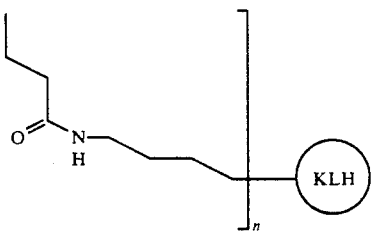

As a further example within this class of reactions, an appropriate hapten in accordance with the principles of the present invention may be synthesized to elicit antibodies which would catalyze the oxidative cleavage of peptides, such as Compound XX in the following example:

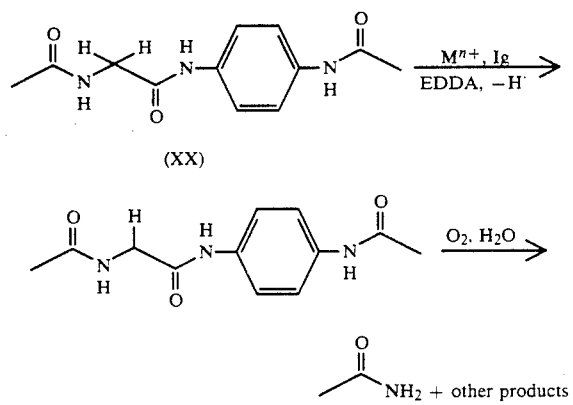

where the metal ion may be Fe or Cu, and EDDA denotes ethylenediamine diacetic acid.

As an example of a reaction involving the reduction of carbonyl compounds performed in accordance with the present invention, in which the antibody causes the reaction to proceed in a stereospecific manner, Compound XXI below is reduced as follows:

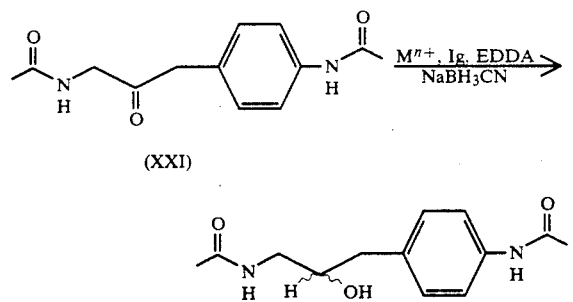

An example of amide bond formation, such as might be employed for a peptide ligation reaction, performed in accordance with the present invention is the ligation of Compounds XXII and XXIII as follows:

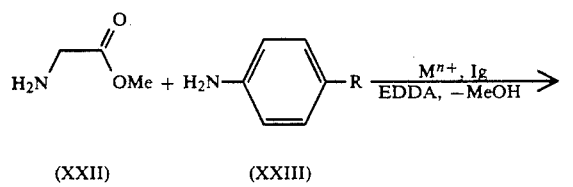

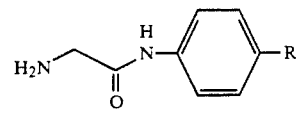

XII. Reactions Involving Pyridoxal and Analogs as Cofactors

A fourth class of reactions to which the present invention is applicable is those involving pyridoxal or any of its derivatives or analogs as cofactors. Examples of pyridoxal-based compounds useful in this class are pyridoxal itself, pyridoxine (pyridoxol) and pyridoxamine. Examples of the types of reactions for which these compounds function as cofactors are racemizations, decarboxylations, transaminations, $\beta$-substitutions, eliminations, and condensations. When used with an apoenzyme, the pyridoxal-based compound is usually in the form of the phosphate, such as for example pyridoxal phosphate, the phosphate group serving to provide the electrostatic binding of the pyridoxal to the apoenzyme. In the context of the present invention, the phosphate group may be included but is not needed, and is preferably excluded.

As in the other reaction classes, the antibody in the present invention serves the function of the apoenzyme, and accordingly has a binding site which includes a region complementary to the pyridoxal-based compound in a conformation which promotes the desired reaction. In preferred embodiments, the binding site recognizes a transition state complex of the pyridoxal-based compound and the substrate. The transition state will vary with the particular reaction being promoted, and in many cases will reflect the selection among a plurality of possible different transition states, different conformations of a transition state, and different orientations of the components in the transition state, needed to favor the desired reaction. For example, the ability to stabilize a carbanionic intermediate may be controlled by the relative conformation of the pyridoxamine group in the antibody combining site. In further cases, either the pyridoxal-based compound or the substrate, or both, may have chiral centers, and the antibody may be used to favor one enantiomer (or combination of enantiomers) over the other(s) by recognizing only the preferred enantiomer(s). In still further cases, stereochemical considerations between the pyridoxal-based compound and the substrate may determine the type of reaction which occurs. In these cases, the antigen binding site will recognize only those transition states in which the components are in the desired orientation, thereby preferentially promoting stereospecific reactions.

The appropriate antibodies in each of these cases are capable of being obtained in various ways. They may for example be elicited by haptens approximating the transition state in the sought-for form (i.e., isomer, enantiomer or stereochemical orientation or conformation). Such haptens may be pure compounds which contain groups or atoms analogous to those of the transition state at critical locations, and thereby approximate the steric and electronic character of the critical atomic groups peculiar to that particular transition state which lies on the reaction pathway leading to the sought-for product. Alternatively, the antibodies may be generated from mixed haptens, and the selection of the appropriate antibody made by conventional antibody screening procedures, such as for instance, growing and isolating clones, then screening by procedures using the reaction itself. Selection of the appropriate method in any given case will be readily apparent to those skilled in the art.

EXAMPLE 4

This example illustrates the preparation of antibodies for the transamination of p-nitrophenylpyruvic acid to p-nitrophenylalanine.

A hapten was formed by first reacting pyridoxal with p-nitrophenylalanine in the presence of aqueous $NaBH_4$ at pH 8.5 to form a stable Schiff base analog. The latter was then treated with thiourea in 48% HBr followed by aqueous ammonium hydroxide to form the disulfide dimer, which was then reduced and subjected to disulfide exchange with a carrier protein to yield a hapten-protein conjugate in which the hapten was the Schiff base analog.

Antibodies were elicited against the conjugate in accordance with conventional procedures, and seven antibodies specifically binding to the hapten itself were selected. Inhibition tests were conducted in which p-nitrophenylalanine and pyridoxamine individually were contacted with the antibodies to determine whether or not binding between the antibodies and the hapten-protein conjugate was inhibited in an ELISA assay. Inhibition was observed to varying degrees in all seven antibodies, suggesting that the antibodies recognized both the cofactor and amino acid portions of the hapten.

To demonstrate enantiomer selectivity, all antibodies were tested for their ability to catalyze the bimolecular condensation of each of the enantiomers D-p-nitrophenylalanine and L-p-nitrophenylalanine individually with 5'-deoxypyridoxal, the latter chosen over pyridoxal to avoid a complicating acetal formation. The progress of the condensation was followed by monitoring the absorbance of the reaction mixture at 430 nm which increases due to aldimine formation (i.e., formation of the condensation product).

With one of the seven antibodies, the half-time for equilibration of the reaction involving the D-isomer was substantially shorter than the half-time for the L-isomer, indicating the enantioselectivity of this antibody for the D-isomer. No such difference was observed using the remaining antibodies. This indicates that enantioselective antibodies can be made and screened.

The same seven antibodies were then used in the transamination reaction between p-nitrophenylpyruvic acid and pyridoxamine to form p-nitrophenylalanine. Reactions were performed in two separate buffer solutions, using 1 mM each of p-nitrophenylpyruvic acid and pyridoxamine, 10 $\mu$M antibody (IgG) and 250 $\mu$M m-nitrobenzylalcohol as an internal standard in each case. The first buffer solution consisted of 10 mM phosphate and 150 mM NaCl at pH 7.5, and the second consisted of 100 mM imidazole and 100 mM NaCl at pH 7.0.

In the phosphate buffer, three of the seven antibodies enhanced the rate of amino acid appearance by approximately a factor of two relative to the same reaction performed in the absence of the antibody. Two of the antibodies strongly favored a side reaction, the oxidative decarboxylation of the keto acid to p-nitrophenylacetic acid, over the transamination. This again demonstrates that highly selective antibodies can be obtained.

In the imidazole buffer, all seven antibodies accelerated amino acid formation by factors ranging from approximately 3 to approximately 10 relative to the same reaction performed without the antibody. Side reactions, including the oxidative decarboxylation of the keto acid to p-nitrophenylacetic acid, were suppressed by all seven antibodies.

Finally, inhibition tests were performed on the antibody which enhanced the bimolecular condensation reaction and the antibody which resulted in the highest rate of amino acid production in the transamination. Each antibody was combined with 100 $\mu$M of the hapten, and in each case, the transamination was noticeably inhibited.

The foregoing is offered primarily for purposes of illustration. It will be readily apparent to those skilled in the art that numerous variations, modifications and substitutions may be made in the procedures, conditions and chemical species described herein, and that the principles described herein may be applied to further reaction classes beyond those described above in detail without departing from the spirit and scope of the invention.

What is claimed is:

1. A method for performing a chemical reaction on a substrate comprising at least one reactant in which said reaction is promoted by contact of said substrate with an auxiliary species which interacts with said reactant but is not joined to said reactant in the product of said reaction, said method comprising:
   (a) contacting in a reaction mixture the following species:
      (i) said substrate,
      (ii) said auxiliary species, and
      (iii) antibody having an antigen binding site which binds to said auxiliary species in a conformation promoting said reaction leading to the product of said reaction; and
   (b) recovering the product of said chemical reaction from said reaction mixture.

2. A method in accordance with claim 1 in which said substrate comprises a single reactant which is converted to a derivative thereof in said reaction.

3. A method in accordance with claim 1 in which said chemical reaction converts said auxiliary species to a modified form.

4. A method for performing a redox reaction on a substrate by conversion of an auxiliary species from a first form which is either an oxidized or a reduced form to a second form which is either a reduced or an oxidized form, respectively, said method comprising:
   (a) contacting in a reaction mixture the following species:
      (i) said substrate,
      (ii) said first form of said auxiliary species, and
      (iii) antibody having an antigen binding site which binds to said auxiliary species in a form promoting said redox reaction leading to the product of said redox reaction; and
   (b) recovering said product from said reaction mixture.

5. A method in accordance with claim 4 in which said auxiliary species is a member selected from the group consisting of nicotinamide-based compounds, flavin-based compounds, pterin-based compounds, ferredoxin-based compounds, thiamine pyrophosphate, pyridoxal-based compounds, ascorbic acid, and complexes of metal ions with porphyrin-based compounds, phthalocyanine derivatives, polypyridyl ligands, aminocarboxylate ligands, linear and cyclic polyamines, and heterocyclic ligands.

6. A method in accordance with claim 4 in which said redox reaction is a reduction reaction selected from the group consisting of:
reduction of carboxylic acids to aldehydes,
reduction of esters to ketones,
reduction of disulfides to thiols,
reduction of sulfoxides or sulfones to sulfides,
reduction of carbonyl compounds to hydroxyl compounds,
reduction of carbonyl compounds to hydrocarbons,
reduction of imines to amines,
stereospecific reductions of carbonyl compounds to imines, and
reductive cleavages.

7. A method in accordance with claim 4 in which said redox reaction is an oxidation reaction, said auxiliary species is flavin, and said antigen binding site binds to 1,5-dihydroflavin.

8. A method in accordance with claim 4 in which said redox reaction is a reduction reaction, said auxiliary species is 1,5-dihydroflavin, and said antigen binding site binds to flavin.

* * * * *